March 10, 1964 C. FISCHER Plant Pat. 2,373
GLADIOLUS PLANT
Filed Jan. 30, 1963
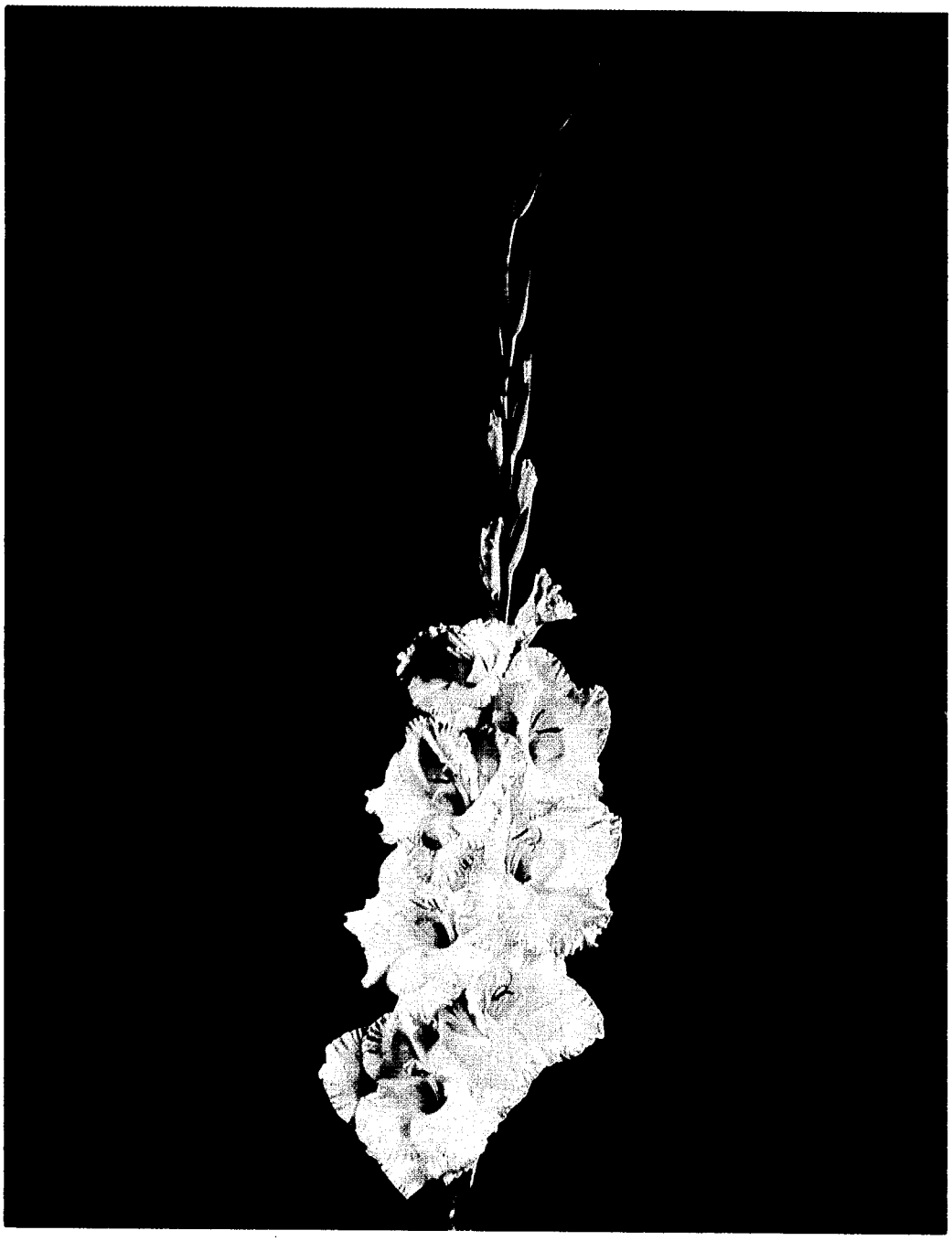
Inventor.
Carl Fischer
By: Robb & Robb
Attorneys.

United States Patent Office

Plant Pat. 2,373
Patented Mar. 10, 1964

2,373
GLADIOLUS PLANT

Carl Fischer, St. Charles, Minn., assignor to Imperial Flowers Limited, Leamington, Ontario, Canada, a corporation of Canada Filed Jan. 30, 1963, Ser. No. 255,139
1 Claim. (Cl. Plt.—85)

The present invention relates to a new and distinct variety of gladiolus plant which was originated by me by crossing the variety known as "Spic and Span" (unpatented) with the variety known as "Friendship" (unpatented), the former being the seed parent and the latter being the pollen parent. This cross was made by me by manual cross-pollination in my breeding fields at St. Charles, Minnesota, as a part of an extensive breeding program seeking to obtain new and improved gladiolus varieties.

The primary objective of this breeding was to produce a commercially satisfactory gladiolus variety which bears flowers of lavender or rose color. This objective was fully achieved, along with other desirable improvements.

As the result of this particular cross, I have produced a new gladiolus variety which is distinguished from its parents, as well as from all other varieties of which I am aware, as evidenced by the following unique combination of features which are outstanding therein:

(1) Ease of production of marketable spikes in abundant quantity;
(2) Robust and vigorous growth;
(3) Good temperature tolerance;
(4) Good disease resistance; and
(5) A distinctive and attractive general color tonality of the flowers corresponding to Phlox Pink color which shades lighter in the heart of the flowers and merging with a large, soft blotch of Mimosa Yellow in the flower throats, and the petals having white midribs.

My new variety resembles the variety known as "Rose Spire" (unpatented) more than any other, but differs principally therefrom by a higher productivity, a habit of being less subject to crooking when growing from large bulbs, an earlier blooming habit, better resistance to Fusarium yellows, a lighter flower color, and larger, more creamy-colored flower throats.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; excellent propagator; average height ranges from about 56 inches to 60 inches.

Blooming habit: Early bloomer in the Northern latitudes of the United States; comes into bloom from large bulbs in about 70 days.

Stems: Straight; willowy.
*Diameter at base.*—About ⅜ inch.
*Color (just above bulb).*—Deep rose purple.

Foliage: Upright; healthy; leaves average from about 34 inches to 36 inches tall and about 1¼ inches wide. Color—green.

Disease resistance: Unusually resistant to Fusarium yellows, Sclerotinia dry rot and Septoria leaf spot, as determined by comparison with other varieties grown in my fields near St. Charles, Minnesota, in irrigated black loam soil.

Corms (bulbs): Round; well husked; extremely healthy. Color of flesh—Straw Yellow, Plate 604/2.

*Flower*

Spike: Willowy; bears from 18 to 20 buds, with from 5 to 7 buds opening at once and 5 or 6 buds showing color.

Bud:
*Size.*—About 3¼ inches long when opening.
*Opening.*—Opens exceptionally well; 5 or 6 buds show color at one time.

Flower:
*Arrangement.*—Florets are arranged informally on the stem and almost always face forward.
*Size.*—Individual florets average about 5 inches in diameter near bottom of spike, with upper florets progressively smaller.
*Form.*—Florets are round and slightly recurved.
*Keeping qualities.*—Keeps well.

Petals:
*Shape.*—Round; neatly ruffled at the edges when well grown.
*Size.*—Outer petals—about 2¼ inches wide. Lip petal—about 1½ inches wide.
*Aspect.*—Average substance.
*Fragrance.*—None.
*Color.*—General color effect is Phlox Pink, Plate 625/2, with edges of petals being Phlox Pink, Plate 625/1 and shading in the heart of the flower to Phlox Pink, Plate 625/3, with a large, soft blotch of Mimosa Yellow, Plate 602/3 in the flower throat, and the petals having white midribs; color of calyx is deep rose-purple.

*Reproductive Organs*

Stamens: Color—light purple.
Pistil: Color—white.

I claim:

A new and distinct variety of gladiolus plant, substantially as herein shown and described, characterized particularly as to novelty by the unique combination of a habit of easily producing marketable flower spikes in abundant quantity, robust and vigorous habits of growth, good temperature tolerance, good disease resistance, and a distinctive and attractive general color tonality of the flowers corresponding to Phlox Pink, said color shading lighter in the heart of the flower and merging with a large, soft blotch of Mimosa Yellow in the flower throats, and with the petals having white midribs.

No references cited.